(12) United States Patent
Venkat et al.

(10) Patent No.: US 10,979,856 B2
(45) Date of Patent: *Apr. 13, 2021

(54) AUTOMATED WORKFLOW ACCESS BASED ON PRIOR USER ACTIVITY

(71) Applicant: CERNER INNOVATION, INC., Kansas City, KS (US)

(72) Inventors: Chandrasekhar Kaiwar Venkat, Leawood, KS (US); Jennifer A. Montag, Kansas City, MO (US); Abhishek Parajuli, Kansas City, MO (US); Stuart Jackson, Kansas City, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 230 days.

This patent is subject to a terminal disclaimer.

(21) Appl. No.: 15/859,582

(22) Filed: Dec. 31, 2017

(65) Prior Publication Data

US 2018/0213361 A1 Jul. 26, 2018

Related U.S. Application Data

(63) Continuation of application No. 14/453,379, filed on Aug. 6, 2014, now Pat. No. 9,955,310, which is a
(Continued)

(51) Int. Cl.
*G16H 40/20* (2018.01)
*H04W 4/029* (2018.01)
(Continued)

(52) U.S. Cl.
CPC ............ *H04W 4/029* (2018.02); *G06N 5/048* (2013.01); *G06Q 10/063118* (2013.01);
(Continued)

(58) Field of Classification Search
CPC ....................................................... G16H 40/20
See application file for complete search history.

(56) References Cited

U.S. PATENT DOCUMENTS 7,676,380 B2 3/2010 Graves et al.
7,707,044 B2 4/2010 Graves et al.
(Continued)

OTHER PUBLICATIONS

Non-Final Office Action received for U.S. Appl. No. 15/836,554, dated Oct. 17, 2019, 19 pages.
(Continued)

*Primary Examiner* — Sheetal R Paulson
(74) *Attorney, Agent, or Firm* — Shook, Hardy & Bacon LLP

(57) ABSTRACT

Systems, methods, and computer-readable media for automating workflow access for a user are provided. A prior activity of a user at a first healthcare application session on a first user device may be determined. The prior activity may occur at a first location in a healthcare facility. Based on the prior activity of the user, as well as a role associated with the user and a second location of the user, a next activity of the user at a second healthcare application session may be predicted. The second healthcare application session may then be automatically launched.

20 Claims, 5 Drawing Sheets

Related U.S. Application Data continuation-in-part of application No. 13/629,983, filed on Sep. 28, 2012, now Pat. No. 9,858,630.

(51) Int. Cl.
    *G06Q 10/06* (2012.01)
    *G06Q 50/22* (2018.01)
    *G06N 5/04* (2006.01)
    *H04W 64/00* (2009.01)
    *H04L 29/08* (2006.01)

(52) U.S. Cl.
    CPC ............ *G06Q 50/22* (2013.01); *G16H 40/20* (2018.01); *H04L 67/12* (2013.01); *H04L 67/14* (2013.01); *H04W 64/00* (2013.01); *H04L 67/20* (2013.01)

(56) References Cited

U.S. PATENT DOCUMENTS

| | | |
|---|---|---|
| 8,127,001 B1 | 2/2012 | Sylvain |
| 8,346,572 B2 | 1/2013 | Eaton, Jr. et al. |
| 8,508,336 B2 | 8/2013 | Giobbi et al. |
| 2006/0185005 A1 | 8/2006 | Graves et al. |
| 2006/0288095 A1* | 12/2006 | Torok .................. G06Q 10/08 709/223 |
| 2007/0234048 A1 | 10/2007 | Ziv |
| 2009/0182577 A1 | 7/2009 | Squilla et al. |
| 2009/0206992 A1 | 8/2009 | Giobbi et al. |
| 2010/0138231 A1 | 6/2010 | Linthicum et al. |
| 2011/0106560 A1 | 5/2011 | Eaton, Jr. et al. |
| 2011/0295616 A1 | 12/2011 | Vesto |
| 2012/0095779 A1 | 4/2012 | Wengrovitz et al. |
| 2013/0173291 A1 | 7/2013 | Kelly et al. |
| 2013/0185772 A1 | 7/2013 | Jaudon et al. |
| 2013/0243275 A1 | 9/2013 | Baym et al. |
| 2013/0260794 A1 | 10/2013 | Prchal et al. |

OTHER PUBLICATIONS

Notice of Allowance dated Feb. 9, 2018 in U.S. Appl. No. 14/453,379, 10 pages.

* cited by examiner

AUTOMATED WORKFLOW ACCESS BASED ON PRIOR USER ACTIVITY

RELATED APPLICATION

This patent application is a continuation and claims priority to U.S. patent application Ser. No. 14/453,379 which as a continuation-in-part of, and claimed priority to, U.S. patent application Ser. No. 13/629,983 (Attorney Docket No. CRNI.174105), filed Sep. 28, 2012, entitled, "Automated Workflow Access Based on Clinical User Role and Location," the disclosure of which is hereby incorporated by reference in its entirety.

BACKGROUND

Patient medical information, such as that contained in a medical record, allows health care providers to provide continuity of care to patients. It is critical for clinicians providing care to patients to review and update each patient's medical record. The growth in access to, and utilization of, electronic medical records by healthcare providers and facilities has significantly reduced the time and organization efforts required by paper medical records. Unfortunately, this growth has introduced new problems. Medical records associated with the incorrect patient are often mistakenly viewed without knowledge by the clinician.

Exacerbating this problem further, clinicians are constantly on the move. For example, clinicians are responsible for patients in multiple healthcare facilities or multiple areas within a single healthcare facility. Each area or each facility may have different software applications or different components within an application supporting various aspects of the clinicians working in those areas or facilities. While making rounds, clinicians are constantly required to log into different devices and applications or change views from within an application to perform their duties. Time spent logging into applications, navigating to the appropriate view or area within an application, and then locating the correct records can adversely impact any efficiency gained by utilizing electronic medical records.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

In brief and at a high level, the present invention provides for automated workflow access for users. Such automated workflow access may include determining a prior activity of a user at a first healthcare application session and, based on that prior activity, predicting a next activity of the user at a second healthcare application session. The prediction may further be based on a role associated with the user and a location of the user. The second healthcare application session associated with the predicted next activity may then be automatically launched. In this way, the present invention may minimize the clicks and/or other user inputs required for a user to navigate to a desired application session corresponding to a particular activity, because the desired application session may be automatically launched. This automated access to the tools and information included in a user's workflow may, among other things, increase the efficiency and accuracy of user activities.

BRIEF DESCRIPTION OF THE DRAWINGS

Embodiments are described in detail below with reference to the attached drawing figures, wherein.

DETAILED DESCRIPTION

Figure 1:
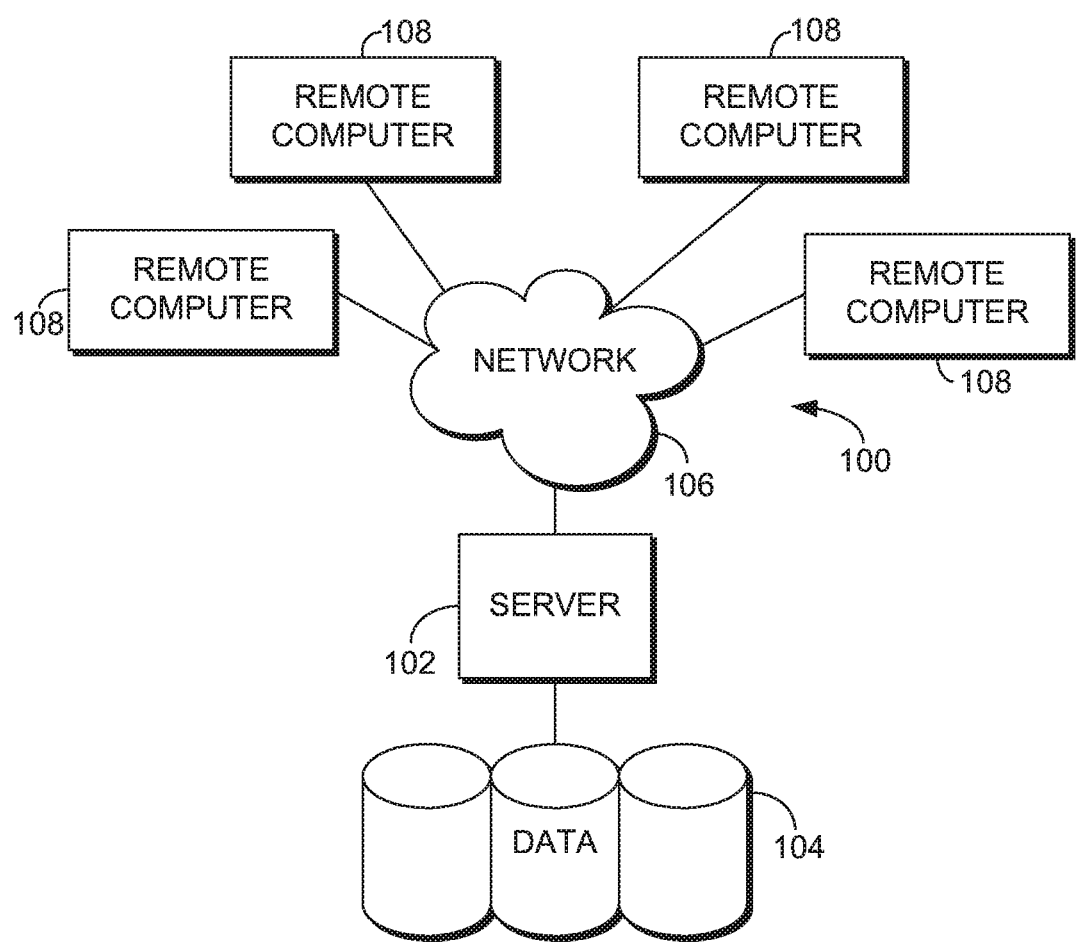
FIG. 1 is a block diagram of an exemplary computing environment suitable for use in implementing embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention relate to methods, systems, and computer readable media for automating workflows based on user roles and locations. Accordingly, one embodiment includes computer storage media having computer-executable instructions embodied thereon that, when executed, facilitate a method of automating workflow access based on user role and location. A location associated with a clinician in a healthcare facility may be detected. A role associated with the clinician authenticated with a first device may be determined. One or more applications associated with the clinician based on the location and the role may be automatically launched on the first device.

In another embodiment, a computer system is provided. The computer system may include a processor coupled to a computer storage medium, the computer storage medium having stored thereon a plurality of computer software components executable by the processor for automating workflows based on user roles and locations. The computer software components may include a detecting component that may detect a location associated with a clinician in a healthcare facility. A role component may determine a role associated with the clinician authenticated with a first device. An application component may launch, on the first device, one or more applications associated with the clinician based on the location and the role. A session component may suspend a session associated with the one or more applications on a first device and resume the session associated with the one or more applications on a second device when the clinician logs into the second device.

In one embodiment, computer storage media having computer-executable instructions embodied thereon that, when executed, facilitate a method of automating workflow access based on user role and location are provided. A role associated with a clinician authenticated to a first device may be communicated from the first device. A workplace including one or more applications associated with the clinician and based on the location and the role of the clinician may be received from a server. The workplace may be displayed on the first device.

Further embodiments are directed to computer-readable media including computer executable instructions for performing a method. The method may include determining a prior activity of a user at a first healthcare application session on a first user device. The prior activity may have occurred at a first location in a healthcare facility. Based on the prior activity of the user, a role associated with the user, and a second location of the user, a next activity of the user at a second healthcare application session may be predicted. The second healthcare application session may be launched.

In yet another embodiment, a computer-implemented method for automating workflow access for a user is provided. The method may include receiving, at a first computing device having a processor and memory, an indication to suspend a first healthcare application session at an exit point of the first healthcare application session. Based on the exit point of the first healthcare application session, a location of the user, and a role associated with the user, a second healthcare application session at an entry point of the second healthcare application session may be automatically launched at a second computing device.

Finally, embodiments of the invention include a computer system for automating workflow access for a user. The computer system may include a processor coupled to a computer storage medium, the computer storage medium having stored thereon a plurality of computer software components executable by the processor. The plurality of computer software components may include a prediction component for predicting a next activity of the user at a healthcare application session based on a prior activity of the user, a location of the user, and a role associated with the user. A device identification component for identifying an appropriate user device associated with the predicted next activity and for indicating a suggestion to engage in the predicted next activity at the appropriate user device may further be included. Additionally, an application component for providing a healthcare application associated with the healthcare application session may be included. Finally, the computer software components may include a session component for launching the healthcare application session at the appropriate user device.

Having briefly described embodiments of the present invention, an exemplary operating environment suitable for use in implementing embodiments of the present invention is described below.

Referring to the drawings in general, and initially to FIG. 1 in particular, an exemplary medical information computing system environment, with which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in association with local and/or remote computer storage media including, by way of example only, memory storage devices.

With continued reference to FIG. 1, the exemplary medical information computing system environment 100 includes a general purpose computing device in the form of a control server 102. Components of the control server 102 may include, without limitation, a processing unit, internal system memory, and a suitable system bus for coupling various system components, including database cluster 104, with the control server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The control server 102 typically includes therein, or has access to, a variety of non-transitory computer-readable media, for instance, database cluster 104. Computer-readable media can be any available media that might be accessed by control server 102, and includes volatile and nonvolatile media, as well as removable and non-removable media. By way of example, and not limitation, computer-readable media may include computer storage media and communication media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage devices, or any other medium which can be used to store the desired information and which may be accessed by the control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 104, provide storage of computer-readable instructions, data structures, program modules, and other data for the control server 102. The control server 102 may operate in a computer network 106 using logical connections to one or more remote computers 108. Remote computers 108 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as intensivists, surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 108 may also be physically located in non-traditional medical care environments so that the entire health care community may be capable of integration on the network. The remote computers 108 may be personal computers, servers, routers, network PCs, peer devices, other common network nodes, or the like, and may include some or all of the elements described above in relation to the control server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the control server 102 may include a modem or other means for establishing communications over the WAN, such as the Internet. In a networked environment, program modules or portions thereof may be stored in association with the control server 102, the database cluster 104, or any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) may be utilized.

In operation, a user, such as a clinician, may enter commands and information into the control server 102 or convey the commands and information to the control server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 102. These commands and information may include input or a trigger (e.g., a user moving from one location to another) from a real-time location system, such as the detection component 212 described herein with respect to FIG. 2. In addition to a monitor, the control server 102 and/or remote computers 108 may include other peripheral output devices, such as speakers and a printer.

Although many other internal components of the control server 102 and the remote computers 108 are not shown, those of ordinary skill in the art will appreciate that such components and their interconnection are well known. Accordingly, additional details concerning the internal construction of the control server 102 and the remote computers 108 are not further disclosed herein.

Figure 2:
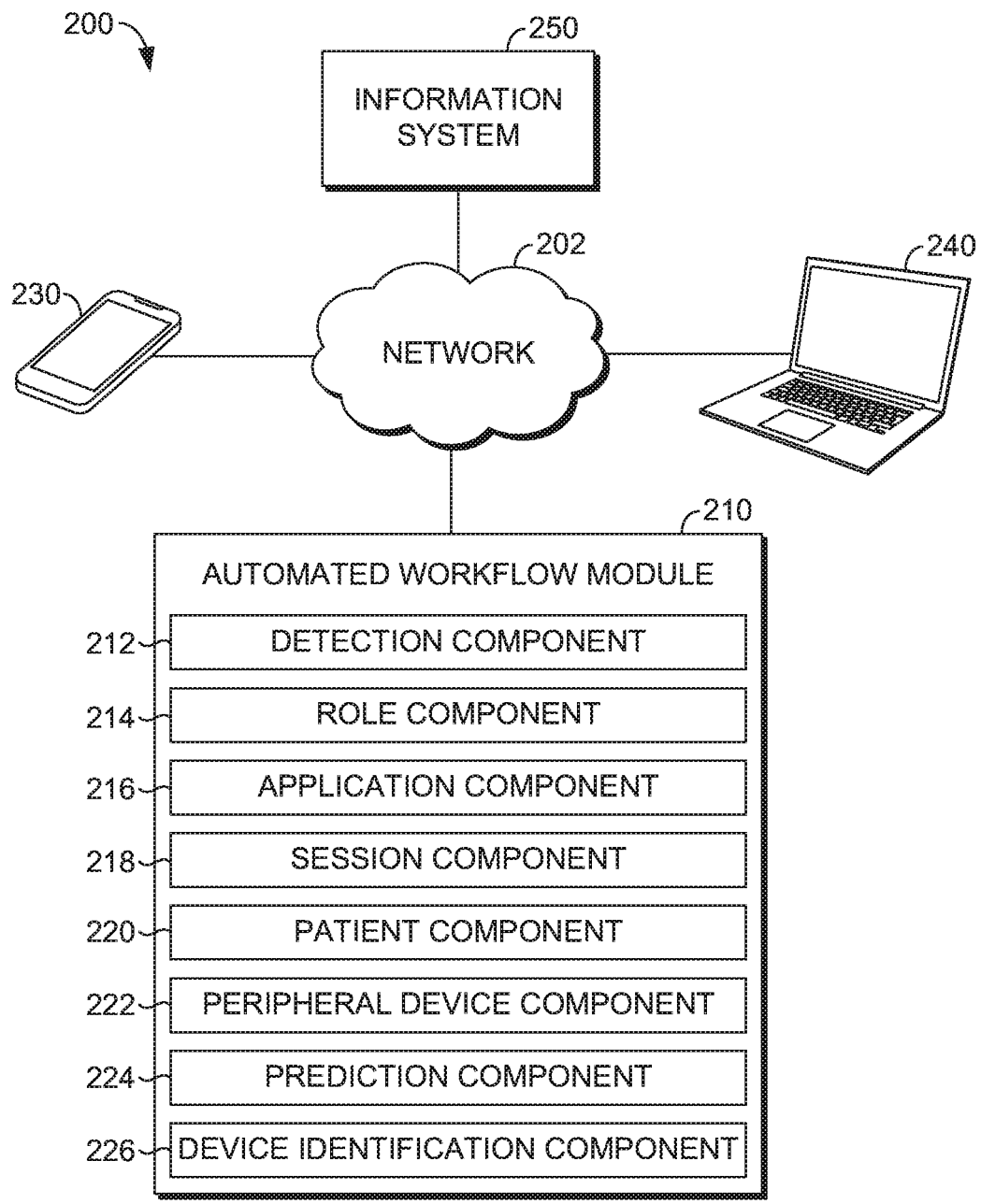
FIG. 2 is an exemplary system architecture suitable for use in implementing embodiments of the present invention.

With reference to FIG. 2, a block diagram is illustrated that shows an exemplary computing system architecture 200 for automating workflows based on user role and location. It will be appreciated that the computing system architecture 200 shown in FIG. 2 is merely an example of one suitable computing system and is not intended as having any dependency or requirement related to any single module/component or combination of modules/components.

The computing system 200 includes network 202, automated workflow module 210, mobile device 230, workstation 240, and information system 250. Although only single instances of the elements are depicted in computing system 200, it should be appreciated that many instances of each of the elements are contemplated and within the scope of the invention. For example, many mobile devices or workstations can be in communication with automated workflow module 210. Similarly, many information systems associated with any number of applications may be in communication with automated workflow module 210. Applications hosted by information system 250 include any application that may be utilized by a user, including a user that is a clinician. For example, information system 250 may include applications supporting email, messaging, browsing, research, electronic medical records, imaging, placing orders, any healthcare related function, and the like. Information system 250 may also include applications supporting admission, discharge, and transfer systems. Information system 250 may further include applications supporting location tracking and proximity detection.

Automated workflow module 210 may reside on one or more computing devices, such as, for example, the control server 102 described above with reference to FIG. 1. By way of example, the control server 102 includes a computer processor and may be a server, personal computer, desktop computer, laptop computer, handheld device, mobile device, consumer electronic device, or the like. Automated workflow module 210 comprises, in various embodiments, detection component 212, role component 214, application component 216, session component 218, patient component 220, peripheral device component 222, prediction component 224, and device identification component 226. In some embodiments, one or more of the components 212, 214, 216, 218, 220, 222, 224, and 226 may be integrated directly into the operating system of a computing device such as the remote computer 108 of FIG. 1. It will be understood that the components 212, 214, 216, 218, 220, 222, 224, and 226 are exemplary in nature and in number and should not be construed as limiting. Any number of components may be employed to achieve the desired functionality within the scope of embodiments hereof.

Detection component 212 may detect a location associated with a user, such as a clinician, in a healthcare facility. In one embodiment, detection component 212 detects location changes associated with the user. In further embodiments, detection component 212 receives location information from a location tracking system. For example, healthcare resources such as clinicians, patients, equipment, clinical devices, and the like may be tracked via a plurality of sensors in the healthcare environment. The sensors in the healthcare environment may utilize ultrasound technology, infrared technology, radio-frequency identification technology, near field communication (NFC) technology, Bluetooth technology, and the like. Using said technology, the sensors may send out signals to clinician identifiers, patient identifiers, item identifiers, clinical device identifiers, or the like. An exemplary sensor system is the Cricket Indoor Location System sponsored by the MIT Project Oxygen partnership. Additionally or alternatively, identifiers associated with the healthcare resources (e.g., clinician identifiers, patient identifiers, item identifiers, clinical device identifiers) may send signals that are detected by a location tracking system. For example, the resource identifiers may send signals that are received by the sensors mentioned above. Any and all such combinations are contemplated as being within the scope of the present invention.

The signals are received by the identifiers and the identifiers respond to the signals. A response from an identifier is received by the sensors and the sensors are able to recognize and determine the location of the responding identifier and, thus, are aware of the resources within the healthcare environment. The respective identifiers associated with the resources may be located, for example, on the person, on the item, or on the device. Exemplary identifiers include badges, wristbands, tags, passive location sensors, and the like. The locations of clinicians, patients, equipment, or the like, associated with a responding identifier, may be detected based on the location of the responding identifier.

In one embodiment, detection component 212 detects a location associated with the user by associating a device the user is logged into with the user's location. The user may log into the device in any number of ways, such as by physically entering log-in credentials or scanning credentials associated with a badge into an input device or touchscreen associated with the device. Or, the user may log into the device by proximity detection, such as with a badge. Detection component 212 may have access to location information regarding various devices in a healthcare facility and, thus, the location of the device may be used to detect the location of the user. For example, if a device is associated with a particular room in the healthcare facility, and the user logs into that device, the user's location may be determined to be that particular room in the healthcare facility.

Turning now to the role component 214, the role component 214 may determine a role associated with a user, such as a role associated with a clinician. The role may be determined by roles or rights assigned to the user's login credentials or to a position or title associated with the user. The role may further be influenced by a location of the user. The location may be a particular area of a single healthcare facility or may be a particular healthcare facility among a plurality of healthcare facilities. For example, a user may have different roles depending on the particular unit within the healthcare facility at which the user is located. Or, the user may have different roles depending on the particular healthcare facility (that may be part of a related or commonly managed network of healthcare facilities) within which a user is making rounds.

Application component 216 may launch one or more applications, such as healthcare applications, associated with a user, such as a clinician, based on the location and the role associated with the user. In one embodiment, the applications are part of a workspace associated with the user. This workspace may include numerous applications that the user accesses during the course of various user activities. In further embodiments, the applications include a patient list for a particular location to assist the user working in that location. The application component 216 may launch one or more patient-specific applications when detection component 212 detects the user's location is a patient-specific location. For example, when the user is in a patient-specific location (e.g., a patient's room), the user does not need access to all of the applications associated with the user's workspace. Rather than launching applications supporting email, messaging, or browsing, application component 216 might only launch applications that are relevant to perform the user's duties in that location for the role associated with the user as determined by role component 214. In another embodiment, application component 216 automatically opens an appropriate application or record within an application. For example, when the user enters a patient's room, if the user does not already have the patient's electronic medical record (EMR) open or even an EMR application open, application component 216 might automatically open the EMR for that particular patient. In this sense, the application state may reflect a change in a user's location, while preserving the application's current session information.

In another embodiment, application component 216 launches one or more non-patient-specific applications when detection component 212 detects the user is in a location where the privacy of a patient or group of patients may be violated. In another embodiment, application component 216 masks identifying data associated with one or more applications so the user can continue working with a particular application even when the user is not in a patient-specific location, or even if the user is in a location where the privacy of a patient or group of patients may be violated. For example, a user may desire to view a chart within a particular patient's record while the user is outside the patient's room (e.g., at a nurse's station, a shared device, or on a mobile device). In order to not reveal the patient's identity to someone who may be passing by, detection component 212 may detect the user is not inside the patient's room or in the user's private office and, in response, might mask, partially mask, hide, obscure, or otherwise remove any identifying information.

Session component 218 may launch a healthcare application session at a device. Launching the healthcare application session may include initiating, loading, running, and/or presenting the application session. A "session," as used herein, may refer to a period of interaction between a user and one or more applications, including a period of interaction between the user and a particular state of the one or more applications. The state of an application may include a particular portion of the application, particular tab, particular record, or other particular item within the application. In one instance, a particular tab with which the user is engaging, such as a tab for ordering images, ordering medications, viewing vitals, viewing lab results, or other tab within an application, may correspond to a state of the application during the application session.

As a further example, when a user opens an application supporting email and begins reading and/or composing emails, the user may be described as engaging in an email application session. When a user closes out of the email application or otherwise terminates interaction with the email application, the corresponding state of the application at the time of such termination may be described as an exit point of the email application session. The exit point may include a particular item or view to which the user has navigated. If the user later resumes interaction with the email application, the session component 218 may automatically launch an email application session at an entry point of the email application session. The entry point may correspond to the state of the application when the application is launched and/or when an application session is resumed. In embodiments, the session component 218 may automatically present an entry point of the email application session that corresponds to the user's most recent exit point of a prior email application session, such that the user need not navigate back to the particular item or view associated with the exit point. In other words, if during a first email application session, a user composes an email to a colleague and the user closes out of the email application prior to completing the email, the state of the application at that time may correspond to an exit point of the email application session. Then, when the user reopens the email application, the session component 218 may automatically present a second email application session with an entry point corresponding to the same email draft that the user was composing at the exit point of the first email application session. While the previous example is presented in the context of an email application session, it will be understood that these features may be implemented in the context of a wide variety of healthcare applications.

In embodiments, the session component 218 suspends a first session associated with one or more applications on a first device (e.g., determines an exit point associated with the first application session) and resumes the session associated with the one or more applications on a second device (e.g., automatically presents an entry point of a second application session that corresponds to an exit point of the first application session) when the user resumes activity at the second device. Resuming activity at the second device may include logging into the second device, or otherwise authenticating the user at the second device. For example, as a clinician walks into a patient's room, the clinician may be reviewing, on a mobile device, a record associated with the patient (e.g., the patient's electronic medical record (EMR), laboratory results, image, etc.). Once the clinician is inside the patient's room, the clinician may desire to log into or authenticate with a workstation or other device in the patient's room. As the clinician logs into or authenticates with that workstation or other device, session component 218 may suspend the session on the mobile device and resume the session on the workstation or other device.

Thus, the present invention is beneficial when, among other things, a user has a particular application open on a first user device, such as a mobile device, and/or when a user has navigated to a particular state, such as a particular item or view within an application, during an application session. Rather than requiring the user to close the application on the first user device, reopen the application on a second user device, such as a workstation or other device (or closing the application on the mobile device and then having to reopen the application within the clinician's workspace), and then navigate to a particular state, such as a particular item or view within the application, session component 218 allows the user to essentially pick up where that user left off within that application session while on the first user device.

In one embodiment, session component 218 suspends a session with the one or more applications on a first device and resumes the session on a second device with one or more applications associated with the second device. In other words, session component 218 may resume the session on the second device, but in embodiments, only resume applications appropriate for the second device and/or a location associated with the second device. Applications that are not included in the resumed session may be suspended until the user logs into another device or is in a location where those applications are needed and/or where those applications are appropriate.

In further embodiments, session component 218 suspends a session on a first device utilizing at least one first device native application and resumes the session on a second device utilizing at least one second device native application. For example, a user may be accessing a patient's chart during a session at a first device. The first device may be an iPad® and the chart may be opened on a native iOS® application. If the user logs into a second device in the patient's room that is running another operating system, such as a version of Microsoft Windows®, the session may be suspended on the first device and resumed on the second device, but with the patient's chart opened in a Microsoft Windows® based EMR application to enable a smooth workflow for the user. Accordingly, a mapping among applications for various devices may be created. For example, an iOS® application may provide a chart application that includes tabs for allergies, patient history, symptoms, labs, medications, orders, and documents. A Windows® application may include tabs for related concepts, but such tabs may include different labels. For example, a "medications" tab in the iOS® application might correspond to a "prescriptions" tab in the Windows® application. A mapping between the iOS® application and the Windows® application may provide a mapping for such related items. Thus, for example, when an exit point of an iOS® application session is within the medications tab, that session may be resumed at an entry point of a Windows® application session within the prescriptions tab. As can be imagined, such mapping may be provided for any number of devices, operating systems, applications, portions of applications, tabs, user interfaces, and any other item, in order to enable continuous, streamlined application sessions among multiple devices. In some instances, the mapping may map equivalent items to one another. In other instances, if an equivalent item is unavailable, the mapping may identify a closest match for a particular item.

Mapping might also be provided among multiple healthcare application providers. For example, a clinician might view a patient EMR within an application supported by a first provider. The clinician may later view the EMR for the same patient within an application supported by a second, different provider. Based on the context (e.g., patient identity) and mapping (e.g., mapping between the first provider's application and the second provider's application), the session component 218 may provide a seamless transition, where the session at the first provider's application is suspended and the session, including an analogous state, according to the mapping, is resumed at the second provider's application. Thus, for example, if the clinician is viewing orders within the first provider's application, the clinician may be automatically presented with orders for the same patient when the clinician switches to the second provider's application.

In embodiments, an indication to suspend a first healthcare application session at an exit point of the first healthcare application session is received at a first computing device. The indication to suspend may include any number of passive and/or affirmative indications that the object of the user's attention is changing. For example, the indication to suspend the first healthcare application may include a user input indicating a command to suspend the first healthcare application session. Such an input may include closing out of the application and/or closing out (e.g., logging out, powering down) of the first computing device, altogether. The input may further include a user gesture indicating a desire to suspend an application session on one device, and resume the session on another device. For example, if the user is engaged in an application session on a mobile phone and wishes to resume the application session on a PC, the user may swipe a finger across the display of the mobile phone in the direction of the PC, in order to indicate that the user wishes to transfer the session from the mobile device to the PC. This may be accomplished using existing swiping and transferring technology. Similarly, NFC technology may allow a user to tap his mobile device to another device in order to provide an indication to suspend the healthcare application session on the mobile device and resume it on the other device.

Additionally or alternatively, receiving the indication to suspend the first healthcare application may include determining that an interaction between the user and the first healthcare application session has ended. As such, an affirmative user input may not be required. For example, a predefined period of inactivity at the first computing device may constitute an indication to suspend. Various technologies may further be implemented for purposes of determining that an interaction between the user and the first healthcare application has ended. For example, gaze detection and/or eye tracking technology may be implemented to detect whether a user's gaze is directed at a device, and thereby determine whether the user's attention is directed to the device. If the user's gaze shifts away from the device, such movement may correspond to an indication to suspend the first healthcare application session. For example, if a user is reviewing information on his mobile device while sitting at a work station that includes a PC, gaze detection technology may be used to determine when the user is reviewing information on his mobile device and when the user sets his mobile device down and begins working on the PC, thereby providing an indication to suspend a first healthcare application session at the mobile device and resume a second healthcare application session at the PC.

Similarly, a change in light detected at the device may correspond to an indication to suspend. For example, if a user is interacting with an application at his mobile device, and then puts his mobile device in his pocket, bag, or other dark location, it may be determined that the interaction between the user and the application session at the mobile device has ended. Changes in position, orientation, acceleration, and other properties associated with the mobile device may also serve as indications to suspend. These properties may be detected by an accelerometer, magnetometer, gyroscope, compass, and other instruments that measure properties such as those mentioned above, in order to determine whether a user has set down, or otherwise discontinued interaction, with a particular device.

In further embodiments, receiving the indication to suspend the first healthcare application session may include a change in the location of the user, such as movement from one location to another location by the user. Additionally, the indication to suspend may include a change from a first computing device to a second computing device, such as a change in the user's attention from the first computing device to the second computing device. For example, a clinician might examine a first patient in that patient's room and engage in corresponding activity at a first healthcare application session on a device. Subsequently, the clinician might move to a second patient's room and engage in activity at a second healthcare application session on the same device. Movement from the first patient's room to the second patient's room may constitute an indication to suspend the healthcare application session and, for example, switch to the second healthcare application session featuring a patient record for the second patient. The fact that the first location is associated with the presence of a first patient and the second location is associated with the presence of the second patient, and that there is a change in the presence of a person at a location associated with the clinician may also constitute an indication to suspend. Additionally or alternatively, the clinician might use a first device in the first patient's room, and switch to a second device in the second patient's room. Such change from the first device to the second device may constitute an indication to suspend the first healthcare application session. The indication to suspend the first healthcare application session may further comprise some combination of a change in location, a change in the presence of a person (e.g., patient) associated with a location, and change in device.

In additional embodiments, based on an exit point of a first healthcare application session, a location of the user, and a role associated with the user, a second healthcare application session at an entry point of the second healthcare application session may be automatically launched. This session may be automatically launched at a second computing device. The entry point of the second healthcare application session may be mapped to the exit point of the first healthcare application session. For example, the second healthcare application session may pick-up where the first healthcare application session left off, thereby providing a continuous healthcare application session experience for the user. As will be discussed in greater detail below, the exit point of the first healthcare application session may also be used to predict a next activity of the user, and the entry point of the second healthcare application session may be based on the predicted next activity of the user.

Turning now to additional components included in the automated workflow module 210, a peripheral device component 222 may provide additional benefits in terms of creating continuous application sessions among multiple devices. In one embodiment, peripheral device component 222 automatically populates a list of available peripheral devices associated with a device. For example, an application may include a print function or some other function that requires the use of a peripheral device. The peripheral device may be directly connected to a device or connected via a network. Each device within a healthcare facility may be associated with different peripheral devices depending on a location within the healthcare facility. When a user's session is resumed at a second device, the peripheral device component 222 may automatically update the resumed session (and each application included therein) with the peripheral device information that is normally associated with the second device, as opposed to maintaining the peripheral device information associated with the first device. This allows, for example, the clinician to print an image or other information to the printer normally utilized by the second device without having to manually configure or select the appropriate printer.

In embodiments, the prediction component 224 works in conjunction with the application component 216 and the session component 218, among other components, to automatically launch a healthcare application session corresponding to a predicted activity of a user. The prediction component 224 may determine and/or analyze a prior activity of the user at a first healthcare application session. Based on this prior activity, the prediction component 224 may predict a next activity of the user. For example, if a user reviews a patient chart during a first healthcare application session, the prediction component 224 may analyze such activity and predict that the user's next activity will involve placing an order for that patient at an application supporting the placement of orders. The application component 216 may automatically launch the appropriate application for this predicted activity, and the session component 218 may automatically launch the appropriate application session.

For purposes of predicting the user's next activity, the prediction component 224 may further rely on location information for a user, such as location information detected by the detection component 212, and/or a role associated with the user, such as a role determined by the role component 214. For example, suppose the user is a doctor, and the doctor uses his mobile device to review high-level information about a patient while walking towards the patient's room. When the doctor enters the patient's room and logs into a device at the patient's room, the prediction component 224 may make a prediction regarding the doctor's next activity, based on the fact that the user is a doctor, the doctor is in a particular patient's room, and the doctor has already reviewed high-level information for that particular patient. Based on all of this information, the prediction component 224 may predict that the doctor does not want to re-review high-level information for the patient, but instead wants to view more detailed and/or complex information for the patient, such as charts, test results, images, and the like. As such, the application component 216 may launch the application corresponding to the predicted activity, and the session component 218 may launch a particular application session, such as a particular portion of the application with which the user is predicted to interact, corresponding to the predicted activity at the device in the patient's room. Thus, for example, when the doctor logs into the device in the patient's room, the doctor may automatically be presented with an application session including charts, test results, images, and the like. As used herein, automatically may describe an event that occurs without user intervention, such as a user input for navigating an application. In the example above, when the doctor is automatically presented with an application session, the application session is presented without intervention by the doctor. In other words, the doctor need not provide further input, such as a mouse click, keyboard stroke, or other user input, in order for the application session to be presented. This is important, because the clicks and/or other user input required to navigate to a desired application session are minimized, thereby increasing user efficiency.

Variations on this example can be imagined, such as where the prediction component 224 makes different predictions based on different user roles, locations, and/or changes in locations. Suppose that in the example above, the user is a nurse instead of a doctor. The nurse may review the same high-level patient information while walking toward the patient's room, but when the nurse logs into the computer in the patient's room, he may be presented with an application session that facilitates the collection of patient information. In other words, the prediction component 224 may predict, based on the fact that the nurse is in the patient's room and has already reviewed high-level information regarding the patient, that the nurse's next activity involves collecting some initial information about the patient, such as weight, blood pressure, description of symptoms, allergy information, etc.

The prediction component 224 may rely on other information, as well, for purposes of making a prediction. For example, information in a patient's EMR may aid in prediction a next activity of a user. Suppose, for instance, that the patient's EMR indicates the patient has high blood pressure. Based on this condition, it may be predicted that a user's next activity will be to order and/or administer medication for this condition. The prediction component 224 may also rely on emails or other notifications sent to a user in order to predict the user's next activity. For example, if a user receives an emergency notification, it may be predicted that a user's next activity will pertain to that emergency, including, for example, a patient, location, or type of treatment associated with the emergency. An appointment schedule may also be a factor in predicting a user's next activity. For example, if a user's schedule includes several appointments with patients, the prediction component 224 may predict that the user's next activities will correspond to that appointment schedule (e.g., examine a first patient at a first time, examine a second patient at a second time).

Returning to the above example where the user is associated with a doctor role, suppose that after leaving the patient's room, the doctor moves toward a work station. Based on the doctor's role, the doctor's previous activity (e.g., meeting with the patient and reviewing detailed patient information), and the doctor's present location at a work station, the prediction component 224 may predict that the doctor's next activity will be to place an order regarding the patient. Such an order might include an order for medication, lab tests, diagnostic imaging, further examination, consultation with a specialist, or any other order for a healthcare-related activity. Thus, when the doctor logs into a computer at the work station, the application component 216 may launch the appropriate application and the session component 218 may launch an appropriate session within the application. Notably, the prediction component 224 may rely not only on current location information for a user, but also on previous location information associated with previous activities, as well as on information relating to a change in location. In this example, for instance, the prediction component 224 may base its prediction not only on the doctor's present location at a work station, but also on the doctor's previous activity at a patient's room and/or on the doctor's change in location from the patient's room to a work station. Such a change in location may indicate that the doctor's next activity is an activity that may not be appropriate for a patient's room. This is just one example of the ways in which information pertaining to location changes may be relevant to predicting a user's next activity.

Continuing with the above example, suppose that after leaving the patient's room, instead of moving toward a work station, the doctor moves toward another patient's room. While walking toward the next patient's room, the doctor may engage his mobile device. The prediction component 224 may predict, based on the doctor's location, that the doctor's next activity is to review high-level information for the next patient. Such a prediction may further be based on an appointment schedule for the clinician. As such, the application component 216 may launch the appropriate application and the session component 218 may launch the appropriate session within the application. In this way, predicting a user's next activity may further be based on a patient associated with a location of the user, and in embodiments, specifically based on the user assessing a patient associated with a particular location. For example, as described above, the prediction component 224 may predict the doctor's next activity is to review high-level patient information based not only on the doctor's location, but also on a particular patient associated with that location (e.g., the high-level patient information that is presented to the doctor is information for the particular patient associated with the doctor's location). The patient component 220 may detect a patient associated with a particular location. Patient component 220 may receive patient location information from an admission, discharge, and transfer system that associates a patient with a location based on admissions, discharges, and transfers. Patient component 220 may further receive patient location information from a tracking system such as the one described herein with respect to detection component 212.

As illustrated in the examples above, the healthcare application session that is launched based on a predicted next activity of the user may be launched on the same device at which the prior activity occurred (e.g., the doctor reviews high-level information for a first patient on the mobile device, and the doctor also reviews high-level information for a second patient on the mobile device), or on a different device (e.g., the doctor reviews high-level information for a first patient on the mobile device, the doctor reviews more detailed patient information at a device in the patient's room, and the doctor places an order at a different device located at a work station). In fact, the prediction component 224 may base its prediction on a type of device at which prior user activity occurred and/or a type of device at which the user is presently engaged, a type of device at which the user is predicted to engage in an activity, and/or a change in the object of the user's attention from one type of device to another type of device. For example, a mobile device may be conducive to checking emails, reviewing high-level patient information, and other activities, but may not be appropriate for reviewing more complex information or engaging in more sophisticated activities. Thus, when a user's prior activity occurred at a mobile device, and the user changes from the mobile device to a work station adapted for more sophisticated activities, the prediction component 224 may predict that the user's next activity will be more complex or sophisticated than the activity at the mobile device. In this way, the prediction component 224 may further rely on a set of form factors associated with various devices at which the user has engaged and/or is engaged in activity. As used herein, form factors may refer to the physical size, shape, and style of a device, as well as the form and layout of its major components. For example, a set of form factors for a mobile device may include a portable configuration, a relatively small display, and limited input capabilities. By contrast, a set of form factors for a device at a work station may include a relatively stationary and/or immobile configuration, a large display, and numerous input capabilities. Based on the form factors associated with a particular device, the prediction component 224 may predict a user activity that is likely to occur at that device.

Also as illustrated in the examples above, a first healthcare application session associated with prior user activity and a second healthcare application session associated with a predicted next activity for the user may both be associated with the same healthcare application. For example, the same application may be associated with the session during which the doctor reviewed high-level patient information for the first patient and with the session during which the doctor reviewed high-level patient information for the second patient. Additionally or alternatively, the first healthcare application session and the second healthcare application session may be associated with different healthcare applications. For example, when the doctor reviewed detailed patient information at a computer in the patient's room during a first healthcare application session, that healthcare application may be different from the healthcare application used during the second healthcare application session to place an order for the patient. The healthcare applications may be provided and/or supported by a variety of healthcare application providers.

In addition to predicting a user's next activity, the prediction component 224 may further make suggestions and/or recommendations to a user based on the predicted next activity. For example, based on the predicted next activity, a user device associated with that activity may be identified, and a suggestion to engage in the predicted next activity at that user device may be made. The device identification component 226 may be configured to identify devices in this way. In embodiments, the device identification component 226 is configured to identify an appropriate user device associated with the predicted next activity and for indicating a suggestion to engage in the predicted next activity at the appropriate user device. As will be explained in more detail below, "appropriate" may refer to the availability of the device, the proximity of the device with respect to the user and/or other locations in the healthcare facility, the compatibility of the device with the predicted next activity, as well as a number of other factors and/or considerations. Suppose, for instance, a user's next activity is predicted to be placing an order for a patient, and that the user is presently engaged in activity at his mobile device. It may be determined that the mobile device is not an ideal and/or appropriate device for placing a patient order. It may further be determined that a device at a work station is appropriate for placing a patient order. Thus, a message indicating a suggestion to place the patient order at a device located at a work station may be presented. Notably, this suggestion may be made automatically, without any user input specifying a next activity or a next device. Additionally or alternatively, it may be determined that the order involves private patient information and, as such, that the relatively public work station may not be appropriate for that activity. A device within an office or other private area may instead be suggested.

Figure 3:
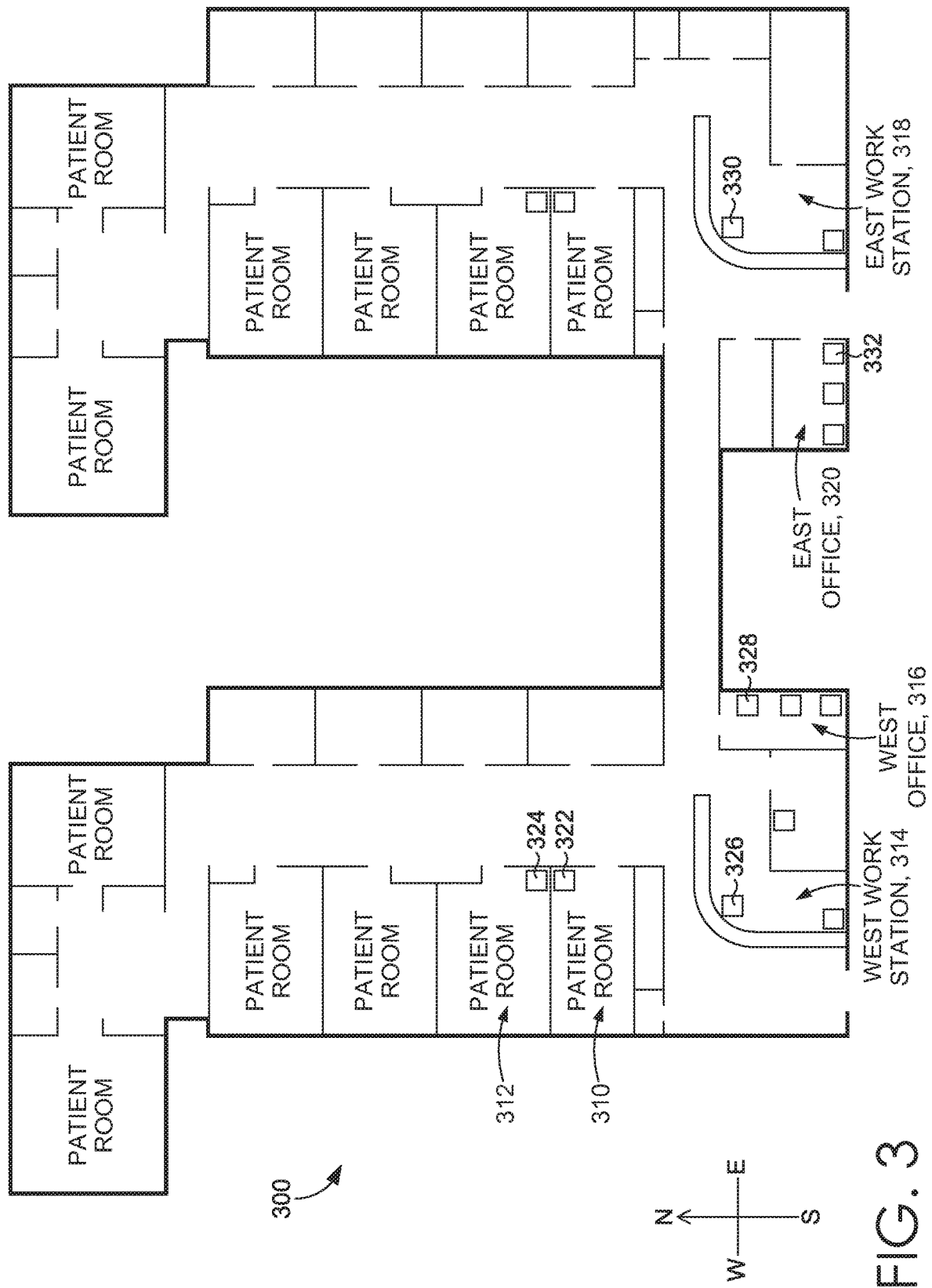
FIG. 3 is a perspective view of an exemplary floor diagram of a healthcare facility, in accordance with an embodiment of the present invention.

This example, as well as other examples involving suggestions and recommendations for a user may be understood with respect to FIG. 3, which provides an exemplary hospital floor diagram 300. The diagram 300 includes a patient room 310, patient room 312, west work station 314, west office 316, east work station 318, and east office 320. Each of these locations includes one or more computing devices, such as devices 322, 324, 326, 328, 330, and 332. These devices may represent any number of computing devices, such as laptops, tablets, mobile devices, computers on wheels, stationary PCs, and any other computing device that may be employed in a healthcare environment. Each device may be associated with a set of form factors, as previously described.

In the context of the hospital floor diagram 300, it can be imagined that a clinician examines a patient in patient room 310, and engages in corresponding activity at computing device 322. If the prediction component 224 predicts that the clinician's next activity will be placing an order for the patient and the device identification component 226 identifies that devices at the west work station 314 are associated with and/or appropriate for this activity, a message may be presented at the computing device 322, and the message may indicate a suggestion that the clinician go to the west work station 314 to place the order. The message may further suggest that the clinician specifically go to computing device 326 at the west work station 314. This suggestion may be based on a proximity, availability, functionality, and/or form factor of the computing device 326. If the devices at the west work station 314 are determined to be unavailable (e.g., the computers are in use, out of order, or otherwise unavailable), a suggestion may be made that the user go to the east work station 318 to place the patient order. The east work station 318 may not be the nearest work station, but it may nonetheless be suggested if it is the nearest work station with devices available for use.

It can further be imagined that the predicted next activity may be associated with private and/or sensitive information. In this case, a suggestion may be made that the clinician go from the patient room 310 to the west office 316 in order to engage in the predicted next activity. In this instance, the suggestion may be based not only on the proximity and availability of the devices in the west office 316, but also on special needs, such as privacy needs, associated with the predicted next activity. If the devices, such as device 328, in the west office 316 are determined to be unavailable or otherwise inappropriate for the predicted next activity, a suggestion to go to the east office 320 may be made.

As illustrated by these examples, suggestions may be made based on any number of factors and/or considerations. For instance, suggestions may further be made based on form factors associated with nearby devices. If a user's next activity is predicted to be viewing a particular type of image, such activity may be possible only at devices having a particular set of form factors. As such, a suggestion may be made corresponding to the nearest available device having the required set of form factors.

Still further, suggestions may relate to a type of activity in which the user should consider engaging. For example, it may be determined that the predicted next activity of the user is not the most efficient activity. This may be due to the proximity and/or availability of devices compatible with that activity, or any other number of factors that may affect efficiency. For example, if the predicted next activity is placing a patient order, but none of the nearby devices associated with that activity are available, a suggestion may be made that the user engage in a different activity until one of the nearby devices associated with ordering activity becomes available.

It should be noted that while the above discussion focuses primarily on the prediction of a user's next immediate move, that the prediction component 224 may also predict a sequence of next activities, or may predict an activity that is likely to occur after some number of intervening activities. For example, suppose it is predicted that the user is going to place a patient order, review a particular type of image, and visit the pharmacy. In this instance, a suggestion may be made that the user engage in these activities in a particular order. If the nearest device configured for viewing the particular type of image is unavailable, but a nearby device for placing a patient order is available, it may be suggested that the user first place the patient order at the nearby device. It may further be determined that a device configured for viewing the particular type of image is located near the pharmacy. Thus, it may be suggested that the user engage in these activities consecutively, in order to optimize the efficiency of the user's activities.

The automated workflow module 210 may include components in addition to those illustrated in FIG. 2 and/or may include fewer components than those illustrated in FIG. 2. For example, in embodiments, the automated workflow module 210 may include a receiving component. The receiving component may be configured to receive an indication to suspend the prior activity of the user, such as an indication to suspend a healthcare application session, as discussed above.

As illustrated by the examples above, user activities, including locations and user roles associated with those activities, may be continuously monitored and/or analyzed. This information may be collected and stored across all devices connected to a network, such as the network 202 of FIG. 2. Such monitoring may be used to develop the logic implemented at the automated workflow module 210. For example, user activities may be monitored and analyzed across all users to develop the prediction logic described above. Additionally, a user's actual activity may be monitored to assess the accuracy of predictions regarding the user's activities. Based on such assessments, the logic used to predict users' activities may be further refined and/or developed. For example, various forms of machine learning may be used to recognize patterns and develop logic models based on those patterns.

Additionally, because data may be collected across all users and all devices at all locations, patterns may be recognized according to user roles, locations, form factors associated with devices, and any other number of factors and/or attributes. Thus, logic may be implemented on a user-specific basis (e.g., a particular user typically engages in a particular series of activities), on the basis of a role associated with a user (e.g., a particular type of user tends to engage in a particular activity), and/or other bases. Furthermore, suggestions and/or recommendations may be made to a user based on the actual activities of users sharing similar attributes (e.g., similar role, similar location). For example, it may be determined that nurses generally navigate to a certain tab in a certain application upon meeting a patient for the first time. Based on this information, a particular nurse may be presented with that tab when he meets a patient for the first time. That particular nurse, however, may prefer that a different tab be presented when he meets with a patient for the first time. Accordingly, the nurse might navigate away from the tab automatically presented, and might instead navigate to his preferred tab. This activity may be monitored and analyzed to determine and assess that particular user's preferences. Additionally or alternatively, the nurse may be automatically presented with his preferred tab, but a message indicating a suggestion that the nurse consider viewing a different tab (e.g., the tab preferred by the majority of nurses). The nurse may then accept or reject that suggestion.

In this way, the logic implemented at the automated workflow module 210 may continuously be updated and/or refined based on actual activities by particular users, as well as patterns observed across various segments of users. As such, it may include the most current information across the general population of users, devices, applications, etc., as well as the most current information for a particular user.

Figure 4:
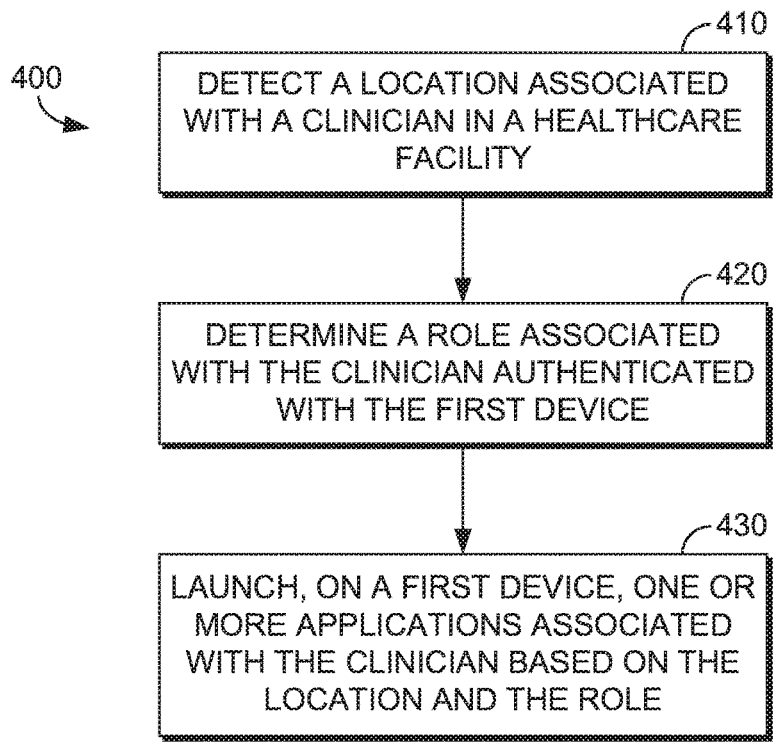
FIG. 4 is an exemplary flow diagram of a method for automating workflow access, in accordance with an embodiment of the present invention.

Referring now to FIG. 4, a flow diagram depicts an illustrative method 400 of automating workflow access based on user role and location, in accordance with an embodiment of the present invention. Initially, at step 410, a location associated with a clinician in a healthcare facility is detected. A role associated with the clinician authenticated with a first device is determined at step 420. One or more applications associated with the clinician based on the location and the role is automatically launched, at step 430, on the first device.

In one embodiment, the location is a non-patient-specific location. For example, the location may be an office associated with the clinician, a shared workstation utilized by clinical staff, a mobile device, and the like. In this example, a clinician may desire to access applications unrelated to a patient. In one embodiment, the one or more applications are non-clinical and/or non-patient-specific applications associated with the location. For example, the clinician may desire access to email, messaging, browser applications, and the like. When a non-patient-specific location is detected, these non-clinical and/or non-patient-specific applications may be included in a workspace associated with the clinician. Further, depending on the particular non-patient-specific location, clinical applications may or may not be included in the clinician's workspace. For example, a clinician may desire to work on clinical applications while in the clinician's office, but due to privacy concerns may not desire to work on clinical applications while on a shared device, in an area accessible to non-medical personnel or non-healthcare facility staff, or on a mobile device. In some of these instances, the clinician may desire to work on clinical applications, but only if patient identifying data is hidden or masked as described above. In various embodiments, the type of applications included in the clinician's workspace is determined by a location and a role associated with a clinician, as well as preferences of the clinician or protocols defined by the particular healthcare facility or as otherwise required.

In one embodiment, the location is a patient-specific location. The patient-specific location may include a patient's room. In one embodiment, the one or more applications are clinical applications associated with the patient-specific location. For example, the applications included in a clinician's workspace when a patient-specific location is detected may include applications related to patient care, such as applications associated with a patient's EMR. Further, the clinician may not have a need for non-clinical applications and these may be excluded from the clinician's workspace in this context.

In one embodiment, an authentication request is received from the clinician for a second device in the healthcare facility. For example, the clinician may be utilizing a mobile device while making rounds. As the clinician enters a patient's room, the clinician may log into or authenticate with a second device, such as an anchor device that is associated with the patient's room. In a another example, the clinician may currently be authenticated with an anchor device in a patient's room, and as the clinician leaves the patient's room, the clinician is automatically logged out of the anchor device and re-authenticated with the mobile device. Similarly, the clinician may encounter a shared workstation, such as at a nurse's station, or a workstation in the clinician's office. The clinician may login to or authenticate with one of those devices.

In one embodiment, after the authentication request is received for the second device, a session associated with the one or more applications on the first device is suspended. As described above, the session may refer to a state of or a placeholder within an application. For example, if a clinician is working within a particular application (e.g., editing data within a particular field of a patient's EMR or viewing a particular area of an image), when the authentication request is received for the second device, that particular state of the application (e.g., the session) is suspended. In one embodiment, the session associated with the one or more applications is resumed on the second device. Whatever state the application or applications were in on the first device are automatically resumed on the second device as if the clinician never switched devices. So, if the clinician were updating a particular field of a patient's EMR or viewing a particular area of an image when the clinician authenticates with the second device, the state of those applications may be resumed on the second device so the clinician can continue updating that particular field of the patient's EMR or viewing that particular area of the image. In other words, the clinician's workspace may open up in the same state, at the same point within an application or applications as it was on the first device (except for peripheral device information which, in one embodiment, is automatically updated to include the appropriate peripheral device information for the second device).

Figure 5:
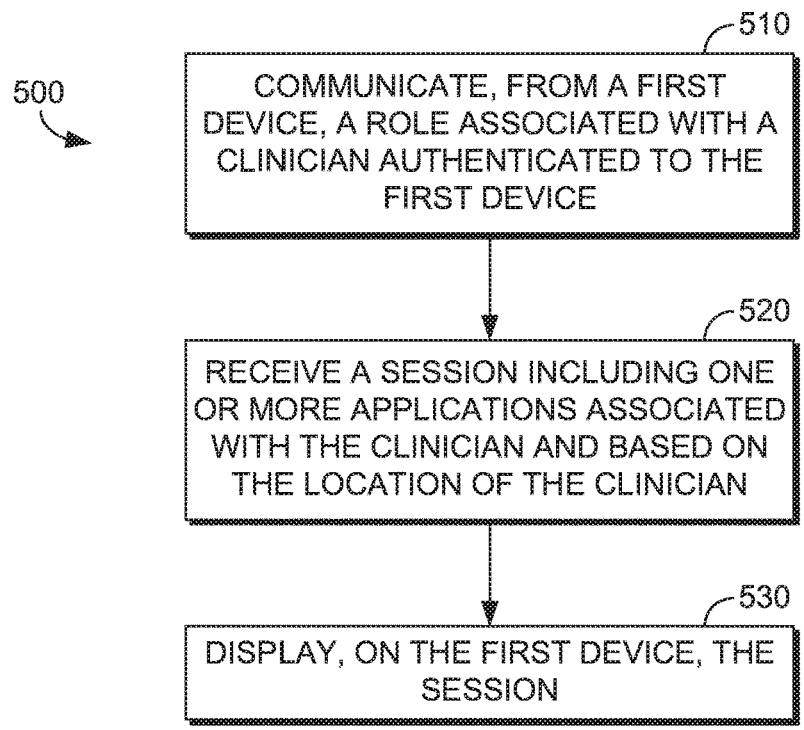
FIG. 5 is an exemplary flow diagram of a method for automating workflow access, in accordance with an embodiment of the present invention.

Referring now to FIG. 5, a flow diagram depicts an illustrative method 500 of automating workflow access based on user role and location, in accordance with an embodiment of the present invention. Initially, at step 510, a role associated with a clinician authenticated to a first device is communicated from the first device. The role may be determined by roles or rights assigned to the clinician's login credentials or to a position or title associated with the clinician. The role may further be influenced by a location of the clinician. The location may be a particular area of a single healthcare facility or may be a particular healthcare facility among a plurality of healthcare facilities. For example, a clinician may have different roles depending on the particular unit within the healthcare facility the clinician is located. Or, the clinician may have different roles depending on the particular healthcare facility (that may be part of a related or commonly managed network of healthcare facilities) a clinician is making rounds.

At step 520, a workplace including one or more applications associated with the clinician and based on a location and role of the clinician are received from a server. The applications may be clinical or non-clinical as described above. Particular functionality or display of the applications may similarly be influenced by the location and role of the clinician. For example, some components of a particular application may be important to one role or location but not another. Accordingly, the components or functionality of a particular application may be limited or enhanced based on these considerations. This increases the efficiency associated with the computing infrastructure of the healthcare facility by providing applications or portions of applications only as needed or desired. The workplace is displayed on the first device at step 530.

In one embodiment, an indication is received that a second device received an authentication request from the clinician. The request signals to the server that the clinician desires to switch devices. In one embodiment, a session associated with the workspace on the first device is suspended. This allows the clinician to view the clinician's workspace in the same state, at the same point within an application or applications as it was on the first device when the session is resumed on the second device. In one embodiment, the workplace and session (e.g., session information) is communicated to the second device. Even though the session is resumed in the same state as it was on the first device, the workplace may include or exclude applications depending on what is appropriate for that location and the role associated with the clinician or for the particular device.

For example, the clinician may be viewing the patient's EMR on a mobile device and also have an email application open. Although both applications are suspended, it would not be appropriate to include the email application in a workspace that is displayed on a particular device type or a particular location, such as an anchor device in a patient's room. Accordingly, only the patient's EMR is included in the workplace (and any other relevant clinical applications). In one embodiment, the session includes peripheral device information associated with the second device.

In one embodiment, an indication is received that the first device received an authentication request. As described above, this can occur automatically when a clinician exits a patient's room or is no longer proximate to a second device. In one embodiment, the workplace and session information is communicated to the first device. Continuing the above example, once the clinician transitions back to the mobile device, the email application is resumed in the clinician's workplace in the same state prior to transitioning from the mobile device to the anchor device.

Figure 6:
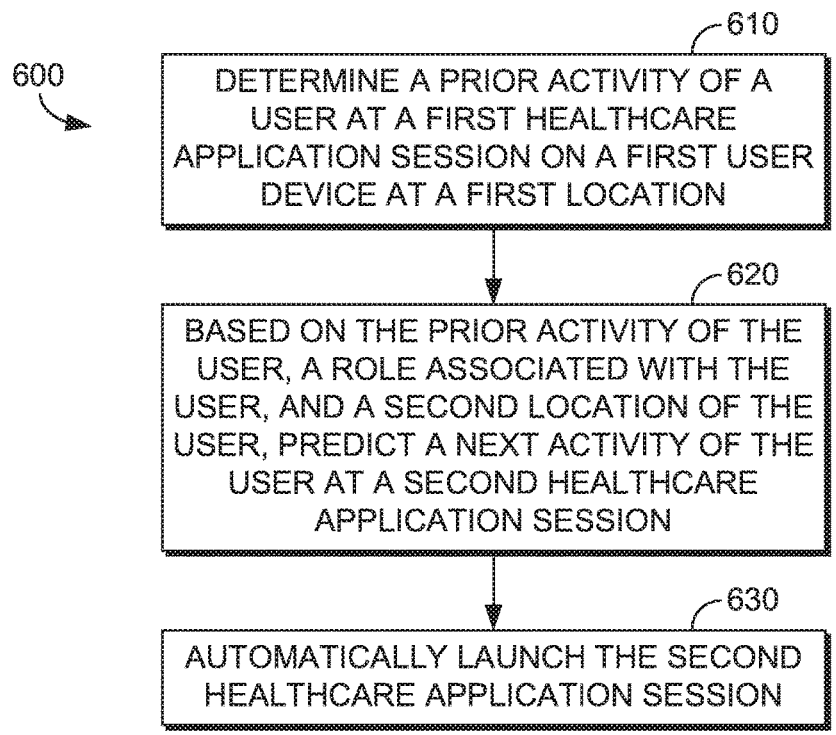
FIG. 6 is an exemplary flow diagram of a method for automating workflow access, in accordance with an embodiment of the present invention.

Turning now to FIG. 6, a flow diagram depicts an illustrative method 600 for automating workflow access. At step 610, a prior activity of a user at a first healthcare application session on a first user device at a first location is determined. Based on the prior activity of the user, a role associated with the user, and a second location of the user, at step 620, a next activity of the user at a second healthcare application session is predicted. The first healthcare application session and the second healthcare application session may be associated with the same healthcare application. Additionally or alternatively, they may be associated with different healthcare applications. The prediction of the next activity of the user may be further based on a number of other items, such as the user moving from the first location to the second location, the user assessing a patient associated with the second location, the user changing from the first user device to a second user device, and/or a set of form factors associated with the first user device and a set of form factors associated with the second user device. At step 630, the second healthcare application session associated with the predicted next activity is automatically launched. The second healthcare application session may be launched on the first user device and/or a second user device.

In embodiments, the method further includes identifying a second user device associated with the predicted next activity of the user and launching, at the first user device, a message indicating a suggestion to engage in the predicted activity at the second user device. Identifying the second user device may be based on a location of the second user device, an availability of the second user device, and/or a set of form factors associated with the second user device. Additionally or alternatively, upon identifying a second user device associated with the predicted next activity of the user, a message indicating a suggestion to engage in an activity different from the predicted next activity may be launched. Such suggestion may be determined and presented based on a location and/or an availability associated with the second device.

Figure 7:
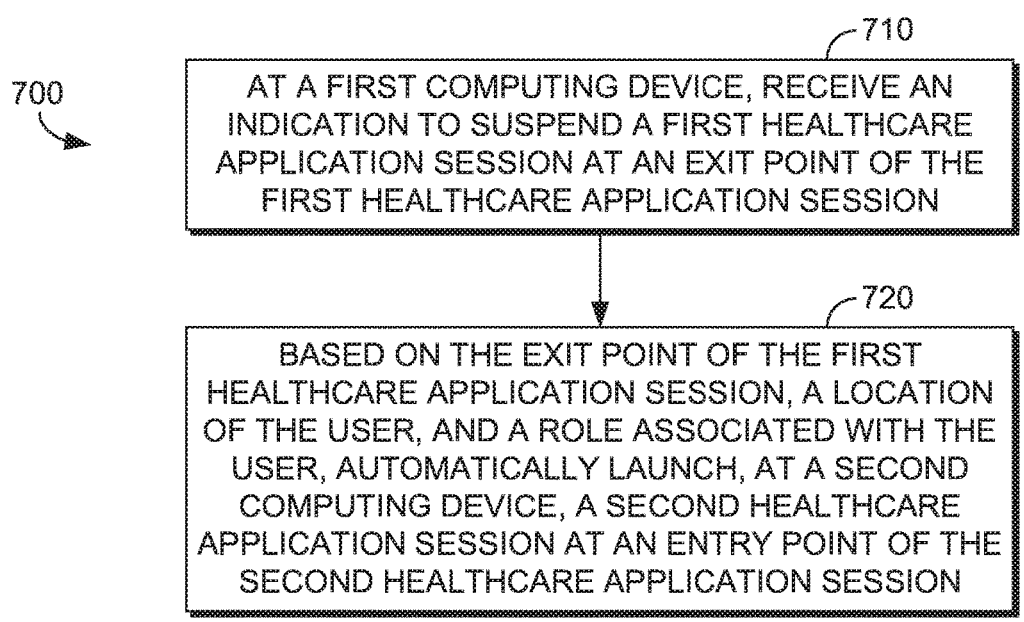
FIG. 7 is an exemplary flow diagram of a method for automating workflow access, in accordance with an embodiment of the present invention.

Referring finally to FIG. 7, a flow diagram depicts an illustrative method 700 for automating workflow access for a user. Step 710 includes receiving, at a first computing device, an indication to suspend a first healthcare application session at an exit point of the first healthcare application session. Receiving the indication to suspend the first healthcare application session may include receiving a user input indicating a command to suspend the first healthcare application session. Receiving the indication to suspend the first healthcare application session may further include determining an interaction between the user and the first healthcare application session has ended. Additionally, receiving the indication to suspend the first healthcare application session may include at least one of a change in the location of the user and a change from the first computing device to a second computing device.

At step 720, based on the exit point of the first healthcare application session, a location of the user, and a role associated with the user, a second healthcare application session is automatically launched at an entry point of the second healthcare application session. The second healthcare application session may be automatically launched at a second computing device. The entry point of the second healthcare application may be mapped to the exit point of the first healthcare application session. In embodiments, the method further includes, based on the exit point of the first healthcare application session, predicting a next activity of the user. In such embodiments, the entry point of the second healthcare application session may be based on the predicted next activity of the user.

Many different arrangements of the various components depicted, as well as components not shown, are possible without departing from the scope of the claims below. Embodiments of the technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations. Such other features and subcombinations are contemplated within the scope of the claims.

The invention claimed is:

1. A computer-implemented method for automating workflow access for a user, the method comprising:
   receiving, at a first computing device having a processor and memory, an indication to suspend a first healthcare application session at an exit point of the first healthcare application session;
   based on the indication to suspend, suspending the first healthcare application session, predicting a next activity of the user, and determining a second computing device associated with the predicted next activity; and
   based on the second computing device being far from a current location of the user or the second computing device being unavailable, providing for presentation a prompt to engage in a different activity at a third computing device and automatically launching, at the third computing device, a second healthcare application session at an entry point of the second healthcare application session.

2. The method of claim 1, wherein the entry point of the second healthcare application session is mapped to the exit point of the first healthcare application session.

3. The method of claim 1, wherein receiving the indication to suspend the first healthcare application session comprises receiving a user input indicating a command to suspend the first healthcare application session.

4. The method of claim 1, wherein the receiving the indication to suspend the first healthcare application session comprises determining an interaction between the user and at least one of the first healthcare application session and the first computing device has ended.

5. The method of claim 1, wherein receiving the indication to suspend the first healthcare application session comprises a user interaction changing from the first computing device to a different computing device.

6. The method of claim 1, further comprising:
based on the exit point of the first healthcare application session, predicting the next activity of the user,
wherein the entry point of the second healthcare application session is based on the predicted next activity of the user.

7. Non-transitory computer storage media storing computer-useable instructions that, when executed by a computing device, cause the computing device to perform operations comprising:
receiving an indication to suspend a first healthcare application session at a first user device, the first healthcare application session associated with a first user activity of a user;
based on the first user activity and on prediction logic, predicting a second user activity of the user;
determining a second user device associated with the second user activity;
based on the second user device being far from a current location of the user or the second user device being unavailable, determining a third user activity at a third user device, wherein the third user activity is different from the second user activity and the third user device is different from the second user device, and providing for presentation a prompt comprising a suggestion for the user to engage in the third user activity at the third user device; and
suspending the first healthcare application session at the first user device and, based on determining the third user activity at the third user device, launching a second healthcare application session at the third user device, the second healthcare application session associated with the third user activity.

8. The computer storage media of claim 7, wherein the prediction logic is developed based on monitoring user activities across a plurality of users and determining patterns in prior activities, roles, and locations among the plurality of users.

9. The computer storage media of claim 7, wherein predicting the second user activity is further based on a change in user location.

10. The computer storage media of claim 7, wherein the prompt further comprises a suggestion to engage in the third user activity at a particular location based on a privacy level associated with the third user activity.

11. The computer storage media of claim 7, wherein predicting the second user activity is further based on an appointment schedule for the user.

12. The computer storage media of claim 7, wherein the operations further comprise preserving an operating state of a particular healthcare application included in the first healthcare application session and causing the second healthcare application session to be launched at the preserved operating state of the particular healthcare application.

13. The computer storage media of claim 7, wherein the operations further comprise masking identifying data presented in the second healthcare application session based on a privacy level associated with the identifying data.

14. The computer storage media of claim 13, wherein masking the identifying data comprises at least one of removing the identifying data or obscuring the identifying data.

15. A computer system comprising:
one or more processors; and
one or more computer storage media storing computer-executable instructions that, when executed by the one or more processors, are configured to implement a method comprising:
receiving an indication to suspend a first healthcare application session at a first user device, the first healthcare application session associated with a first user activity of a user;
based on the first user activity and on prediction logic, predicting a second user activity of the user;
determining a second user device associated with the second user activity;
based on the second user device being far from a current location of the user or the second user device being unavailable, determining a third user activity at a third user device, wherein the third user activity is different from the second user activity and the third user device is different from the second user device, and providing for presentation a prompt comprising a suggestion for the user to engage in the third user activity at the third user device; and
suspending the first healthcare application session at the first user device and, based on determining the third user activity at the third user device, launching a second healthcare application session at the third user device, the second healthcare application session associated with the third user activity.

16. The computer system of claim 15, wherein the prediction logic is developed based on monitoring user activities across a plurality of users and determining patterns in prior activities, roles, and locations among the plurality of users.

17. The computer system of claim 15, wherein predicting the second user activity is further based on a change in user location.

18. The computer system of claim 15, wherein the prompt further comprises a suggestion to engage in the third user activity at a particular location based on a privacy level associated with the third user activity.

19. The computer system of claim 15, wherein predicting the second user activity is further based on an appointment schedule for the user.

20. The computer system of claim 15, wherein the method further comprises preserving an operating state of a particular healthcare application included in the first healthcare application session and causing the second healthcare application session to be launched at the preserved operating state of the particular healthcare application.

* * * * *